United States Patent [19]
Everett

[11] Patent Number: 5,351,644
[45] Date of Patent: Oct. 4, 1994

[54] METHOD OF BOVINE HERD MANAGEMENT

[75] Inventor: Robert W. Everett, Freeville, N.Y.

[73] Assignee: Cornell Research Foundation, Ithaca, N.Y.

[21] Appl. No.: 23,244

[22] Filed: Feb. 25, 1993

[51] Int. Cl.$^5$ .............................................. A01K 29/00
[52] U.S. Cl. .................................. 119/14.01; 119/840
[58] Field of Search .............. 119/14.01, 14.02, 51.01, 119/155, 174

[56] References Cited

FOREIGN PATENT DOCUMENTS

| | | | |
|---|---|---|---|
| 923476 | 4/1982 | U.S.S.R. | 119/14.01 |
| 1591900 | 9/1990 | U.S.S.R. | 119/14.01 |
| 1658949 | 6/1991 | U.S.S.R. | 119/174 |
| 1664205 | 7/1991 | U.S.S.R. | 119/14.01 |

*Primary Examiner*—Robert P. Swiatek
*Attorney, Agent, or Firm*—Salzman & Levy

[57] ABSTRACT

A method of bovine herd management based upon a dynamic mathematical model. The method gathers data on milk production on a periodic or routine basis for each cow in the herd. The data includes factors denoting both the quantity and the quality of the milk being produced. A database for each cow is established and continuously updated. A mathematical herd management model is used to establish the database, wherein the gathered data is then modified and used to interpret and determine the actual productivity of each cow in the herd for that test day. Using this data, a manager of the herd can then breed those cows having a capability superior to their associates in the herd. Likewise, the less productive members of the herd can be culled or eliminated from the herd. Another aspect of the invention includes the use of the database to quantitatively assess the effect of change, including changes made in formulas, in environmental conditions and in breeding practices. Thus, for the first time, herd management can be scientifically controlled on a quantitative basis. Genetic evaluations can be made from the databases of many herds in order to select primary A-1, bulls capable of siring daughters in many herds. For maximum efficiency, databases of many herds can be combined or linked across the entire nation.

14 Claims, No Drawings

METHOD OF BOVINE HERD MANAGEMENT

FIELD OF THE INVENTION

The present invention pertains to the management of a bovine herd and, more particularly, to a dynamic, mathematical technique for periodically analyzing and upgrading individual milk production databases. The ultimate goal of the method is the maximization of milk production, whereby the best lactating constituents of the herd are determined and bred. Less productive bovines are quickly recognized and subsequently culled from the herd in order to maximize the herd's production. Utilizing databases of many herds, genetic evaluations can be made in order to select primary A-1 bulls having daughters in many herds. For maximum efficiency, databases of many herds can be combined or linked across the entire nation.

BACKGROUND OF THE INVENTION

The raising of bovine herds for milk production is an industry that has its roots in antiquity. Many influential factors must be considered in determining whether a particular herd of cows will be productive, i.e., provide large quantities of high-quality milk. Environmental elements, for example, affect each cow separately, as well as the herd as a composite. Factors such as season, parity, age, pregnancy and the number of days dry also affect the overall quantity and quality of a cow's milk with respect to fat, protein, water content and somatic cell content. Additionally, the introduction of new members to the herd (e.g., when a calf is born) shifts the disposition and functioning of the overall herd.

Many studies have been conducted and models created for maximizing a herd. Most such prior models are based upon a theoretical, standard production curve that averages a global herd population. This so-called "average" curve does not actually predict the production for any given herd composite; rather, it serves as a standard by which one could make a comparison of the relative merits of a particular cow or herd in question.

A particular bovine herd cannot ever conform to any theoretical curve. Each herd is unique. It cannot follow any set criteria, since it is a living, changing, shifting entity. New members enter periodically, and old members leave. With each cow at a particular point in its lactating development and production, there are both good and poor producers in a herd.

Prior management techniques could only suggest in a general sense whether changes were required. They could only provide a qualitative assessment of any particular change in a management scheme.

The present invention has developed a new, accurate herd management method based on a constantly evolving, dynamic management model. Control of the herd is continually being analyzed and upgraded. Changes in the herd are made periodically on a running basis. Production curves for each member of the herd are constantly being reformulated, analyzed and compared with individual past performances, as well as the performance of the overall herd.

The mathematic model of the invention uses test-day milk production analyses for each cow in the herd and introduces parameters affecting that particular day's milk production. At any particular time, milk production will be influenced by factors such as days in pregnancy, age, freshening, position within the lactation curve, etc. Utilizing milk quantity and quality data for each particular cow in the herd, over time, a "milk production capability" database begins to evolve for each individual member thereof. It becomes quantitatively evident over time that some cows in the herd are genetically better milk producers than others. These superior producers are then bred, with the inferior cows culled from the herd. In this fashion, the invention maximizes the herd's milk production on a continual basis.

Another aspect of the invention allows for the analysis of different conditions that affect milk production as they are introduced. For example, once a sufficient database is established for a particular herd, the manager of the herd may periodically change the feed to assess which feed formula produces the best results. Likewise, changes in housing, spacing, temperature and other environmental conditions can be quantitatively assessed as to their effect(s) upon milk production.

For the first time in breeding history, the dynamic mathematic tool of the invention provides precise, specific quantitative measurement of the effects of changes upon a herd's production. This represents a new and more complete analysis; heretofore, such analysis could only be assessed qualitatively.

SUMMARY OF THE INVENTION

In accordance with the present invention, there is provided a method of bovine herd management based upon a dynamic mathematical model. The method gathers data on milk production on a periodic or routine basis for each cow in the herd. The data includes factors denoting both the quantity and the quality of the milk being produced. A database for each cow is established and continuously updated. A mathematical herd management model is used to establish the database, wherein the gathered data is then modified and used to interpret and determine the "actual productivity" of each cow in the herd for that test day.

"Actual productivity" is defined herein as that milk production for an individual cow at a particular point in time, with respect to average production data established for that cow over time minus individual adjustment factors determined from the herd database.

The mathematical herd management model contains equations that produce these individual adjustment factors or parameters that account for the changes in an individual cow's productivity. Such changes result from effects based upon age, pregnancy, position on the lactation curve, the month of freshening and other random and fixed parameters associated with the biology of an individual cow. The "actual production" of each cow is thus determined, and deviations from the norm are easily recognized. Calculations made in accordance with these equations eliminates approximately forty percent of the variation in test-day production data. Thus, the invention produces a database for each cow in the herd that reflects, in the true sense, the capability of that cow to produce milk.

Using this data, a manager of the herd can then breed those cows having a capability superior to their associates in the herd. Likewise, poor-producing members of the herd can be culled or eliminated therefrom.

Another aspect of the invention includes the use of the database to quantitatively assess the effect of change; some examples thereof are changes made in feed formulas, changes in environmental conditions and changes in breeding practices. Thus, for the first time, herd management can be scientifically controlled on a quantitative basis. Genetic evaluations can be made from the databases of many herds in order to select primary A-1 bulls capable of siring daughters in many herds. For maximum efficiency, databases of many herds can be combined or linked across the entire nation.

It is an object of this invention to provide an improved method of bovine herd management.

It is another object of the invention to provide a method of herd management that assesses the "actual productivity" of each cow in a herd.

It is yet another object of this invention to provide a technique by which milk production can be quantitatively assessed for each member in a bovine herd.

It is a further object of the invention to provide a method by which a herd of cows can be bred for maximum milk production.

It is but another object of this invention to provide a technique by which changes to the herd management scheme can be quantitatively assessed with respect to milk production.

It is yet a further object of the invention to provide genetic evaluations from generated databases of many herds, in order to select primary A-1 bulls having daughters in many herds.

It is still another object of this invention to provide genetic evaluations from generated databases of many herds, with the linking or combining of the database information on a regional or nationwide basis.

These and other objects of the invention will become more apparent and better understood with reference to the subsequent detailed description.

DESCRIPTION OF THE PREFERRED EMBODIMENT

Generally speaking, the invention features a new method of herd management wherein "actual" milk productivity of individual members of a herd can be quantitatively assessed. The raw milk productivity data is modified by a mathematical, test-day model developed in accordance with this invention. The test-day model adjusts the milk production data for the individual conditions of each cow, whereby 40% of the variation in production data is removed. This data is then compiled for each member of the herd on a continual basis, with the data being routinely updated. Information on many herds can be linked or combined to provide genetic evaluations of the best bulls and best milk-producing cows traversing many herds. These generated databases can be linked nationwide for maximum milk productivity.

The general, mathematical test-day formula of the invention is given in equation (1) below:

$$Y_{ijklmn} = H_i + A_j + D_k + P_l + F_m + e_{ijklmn} \quad (1)$$

Where:

$Y_{ijklmn}$ is a vector of test-day observations for a cow whose test-day milk is tested for protein, fat, water and somatic cell content;

$H_i$ is a fixed effect of the $i^{th}$ test-day within the herd;

$A_j$ is a fixed effect of the $j^{th}$ age of the cow when observed on test-day;

$D_k$ is a fixed effect of the $k^{th}$ days in milk (position on the lactation curve) when observed on test-day;

$P_l$ is a fixed effect of the $l^{th}$ days in pregnancy of the cow when observed on test-day;

$F_m$ is a fixed effect of the $m^{th}$ month freshening of a cow when observed on test-day; and $e_{ijklmn}$ are random residuals, with (co) variance structure R.

The random residuals "e" for a cow are obtained by subtraction and are combined to produce an n-day lactation, where "n" is usually 305 days of production per year, but can be any number of days, and production for an n-day lactation is obtained from the formula:

$$\hat{t}_n = 1'RM(MRM)^{-1} \hat{e} \quad (2)$$

Where:

$\hat{t}_n$ is the sum of the "n" day residuals, producing an n-day lactation as a deviation with mean zero;

R is the residual covariance matrix;

M is a mapping incidence matrix of the observed test-day of the "n" possible test days; and $\hat{e}$ is the vector of residuals $(y - X_i\hat{B})$.

The mathematical model of this invention is based on the concept that, by removing approximately forty percent (40%) of the variation in the test-day production data, "actual production" values are obtained. These values enable the keeping of n-day records of much greater value. To summarize, these production data are adjusted for:

(a) age within the herd
(b) pregnancy within the herd
(c) days in milk within the herd
(d) month freshening within the herd
(e) changes in herd management over time.

Equation (1) is of great value to dairy herd management, because the estimate of the fixed effects are not determined anywhere in the world. The parameters influencing these estimates have never been accounted for in prior art estimates. The estimates are based on actual herd data, rather than a theoretical, total global population. Data derived by the invention has a correct statistical variance that is lacking in the prior methods. The invention will provide for the evaluation of new technologies that will be adopted on dairy farms in the future. A true quantitative assessment can be made as to the effects of all changes made in herd management. Most importantly, the inventive method allows for genetic assessment of those constituents in the herd having the greatest milk-producing value. This genetic assessment can be stretched over wide populations and many herds, thus increasing its potential value to a maximum efficiency. This invention makes possible the keeping of linked and compiled databases across the entire nation.

EXAMPLE

An example of the method of the invention using the mathematical model is presented below with respect to the following TABLE of data.

TABLE

| Cow | Milk Production (lbs) | Test Day | Age (mos.) | Days in Milk |
|-----|----------------------|----------|------------|--------------|
| 1 | 75 | 1 | 24 | 10 |
| 1 | 70 | 3 | 25 | 30 |
| 1 | 65 | 4 | 26 | 60 |
| 2 | 85 | 2 | 24 | 10 |
| 2 | 70 | 3 | 25 | 40 |
| 2 | 80 | 4 | 26 | 70 |
| 3 | 80 | 1 | 24 | 10 |
| 3 | 75 | 2 | 25 | 40 |
| 3 | 70 | 3 | 26 | 60 |
| 4 | 65 | 1 | 24 | 10 |

TABLE-continued

| Cow | Milk Production (lbs) | Test Day | Age (mos.) | Days in Milk |
| --- | --- | --- | --- | --- |
| 4 | 65 | 2 | 25 | 40 |
| 4 | 70 | 4 | 26 | 70 |

Assume the model is:

$Y_{ijkl} = \text{Test-day}_i + \text{Age}_j + \text{Days in Milk}_k + \hat{e}_{ijkl}$ Where:
$Y_{ijkl}$ is milk production on test-day "i" for a cow of age "j" that was "k" days in milk;

Test-day$_i$ is the effect of herd management in this herd on test day "i" which is constant and unknown for all cows (a fixed effect);

Age$_j$ is the effect of age in months, which is constant and unknown for all cows in this herd that are "j" months old;

Days in Milk (DIM)$_k$ is the effect of the stage of lactation that is constant and unknown for all cows in this herd "k" days in milk; and "$\hat{e}_{ijkl}$" is the error or residual that is unexplained by test-day, age and days in milk.

The matrix notation for this data can be written as follows:

$$X'R^{-1}X\hat{B} = X'R^{-1}Y \quad (3)$$

Where:
X is an incidence matrix describing the test days, age and days in milk for each record on each cow;

R is the residual (co)variance matrix which describes the (correlation) relationships between one test day and the next with a cow;

Y is the milk observation in vector form; and $\hat{B}$ is a vector of solutions which is of primary interest.
$\hat{B}$ can be obtained by:

$$\hat{B} = (X'R^{-1}X)^{-1}(X'R^{-1}Y) \quad (4)$$

The residuals are defined by e:

$\hat{e} = Y - X\hat{B}$ which are deviations from expected production within the herd Utilizing the data for the four cows of the TABLE, Y is given by:

$$Y = \begin{bmatrix} 75 \\ 70 \\ 65 \\ 85 \\ 70 \\ 80 \\ 80 \\ 75 \\ 70 \\ 65 \\ 65 \\ 70 \end{bmatrix}$$

$$X = \begin{bmatrix} t_1 & t_2 & t_3 & t_4 & A_{24} & A_{25} & A_{26} & D_{10} & D_{40} & D_{70} \\ 1 & 0 & 0 & 0 & 1 & 0 & 0 & 1 & 0 & 0 \\ 0 & 0 & 1 & 0 & 0 & 0 & 1 & 1 & 0 & 0 \\ 0 & 0 & 0 & 1 & 0 & 0 & 1 & 0 & 1 & 0 \\ 0 & 1 & 0 & 0 & 1 & 0 & 0 & 1 & 0 & 0 \\ 0 & 0 & 1 & 0 & 0 & 1 & 0 & 0 & 1 & 0 \\ 0 & 0 & 0 & 1 & 0 & 0 & 1 & 0 & 0 & 1 \\ 1 & 0 & 0 & 0 & 1 & 0 & 0 & 1 & 0 & 0 \\ 0 & 1 & 0 & 0 & 0 & 1 & 0 & 0 & 1 & 0 \\ 0 & 0 & 1 & 0 & 1 & 0 & 0 & 1 & 0 & 0 \\ 1 & 0 & 0 & 0 & 1 & 0 & 0 & 1 & 0 & 0 \\ 0 & 1 & 0 & 0 & 0 & 1 & 0 & 0 & 1 & 0 \\ 0 & 0 & 0 & 1 & 0 & 1 & 0 & 0 & 0 & 1 \end{bmatrix}$$

$$R = \begin{bmatrix} .73 & .73^2 & .73^3 & 0 & \cdots & \cdots & 0 & 0 & 0 \\ .73^2 & .73 & .73^3 & 0 & \cdots & \cdots & 0 & 0 & 0 \\ .73^3 & .73^2 & .73 & 0 & & & 0 & 0 & 0 \\ 0 & 0 & 0 & .73 & & & 0 & 0 & 0 \\ \cdots & \cdots & \cdots & \cdots & \cdots & 0 & .73 & .73^2 & .73^3 \\ \cdots & \cdots & \cdots & \cdots & \cdots & 0 & .73^3 & .73 & .73^2 \\ 0 & \cdots & \cdots & \cdots & \cdots & 0 & .73^3 & .73^2 & .73 \end{bmatrix} \sigma e^2$$

Cow No. 1 ... etc, ... Cow No. 4

The first row of the X matrix describes Cow No. 1's production of 75 lbs. that was observed at test 1, age 24 and days in milk 10.

The R matrix describes the correlations among test day observations. Observations are correlated within a cow, but are uncorrelated from cow No. 1 to cow No. 2, etc.

$\sigma e^2$ is the residual variance which, for most herds, is approximately $13^2$ pounds of milk.

$R\sigma e^2$ is the residual covariance matrix which is correlations times error variance.

After the aforesaid matrix manipulations, solutions for B were calculated according to equation (4), as follows:

$$\hat{B} = \begin{bmatrix} 76.65 \\ 85.52 \\ 80.90 \\ 77.01 \\ 7.64 \\ -1.31 \\ 0 \\ -10.35 \\ -12.57 \\ 0 \end{bmatrix} \begin{matrix} t_1 \\ t_2 \\ t_3 \\ t_4 \\ A_{24} \\ A_{25} \\ A_{26} \\ D_{10} \\ D_{40} \\ D_{70} \end{matrix}$$

Constraints were placed on the equations: $A_{26} = D_{70} = 0$. Residuals for each milk weight are:

$$\hat{e} = Y - X\hat{B} \quad (5)$$

and for the first test on cow No. 1, this is:

$\hat{e} = 75 - 76.65 - 7.64 - (-10.35) = +1.06$

In other words, cow No. 1 produced 1.06 lbs. above expectation. On test day 1, the manager's ability or management program is estimated at 76.65 lbs. of milk per cow per day. ($t_1 = 76.65$). It is noted here that this example is small and, for brevity and simplicity, does not include all of the variables in the model. The model of the invention will become more complex as additional parameters are added. However, the mathematics does not change.

The following references teach the mathematical calculations supporting the model of the invention. The R matrix is described by C. R. Henderson. Reference is made to its use in Searle 1971; and examples of general equations are given by Searle 1966, pages 254 through 259.

REFERENCES

Henderson, C. R., 1984. *Applications of Linear Models in Animal Breeding.* University of Guelph; Guelph, Ontario, Canada; Catalogue code SF 105.H46 1984.

Graybill, Franklin A., 1961. *An Introduction to Linear Statistical Models.* McGraw-Hill Book Company, Inc.; New York, Toronto, London.

Searle, S. R., 1966. *Matrix Algebra for the Biological Sciences.* John Wiley and Sons, Inc.; New York, London, Sydney; Card Catalogue No. 66-11528.

Searle, S. R., 1971. *Linear Models.* John Wiley and Sons, Inc.; New York, London, Sydney; Card Catalogue No. 70-138919.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention. Having thus described the invention, what is desired to be protected by Letters Patent is presented in the subsequently appended claims.

What is claimed is:

1. A method of bovine herd management comprising the steps of:
   a) gathering test-day data on milk production for each member of a herd on a routine basis;
   b) using a mathematical herd management model to modify the test-day data to determine the actual productivity of each cow in the herd;
   c) establishing a database for each member of said herd, based upon the modified data of step (b);
   d) continuously updating said database; and
   e) making physical changes to said herd based upon information in said database, in order to increase milk productivity of said herd.

2. The method of herd management in accordance with claim 1, wherein the gathering of data of step (a) includes obtaining quantitative and qualitative milk production data for each member of a herd on a routine basis.

3. The method of herd management in accordance with claim 2, wherein said gathering of data on a routine basis includes test-day information.

4. The method of herd management in accordance with claim 1, wherein the modified data of step (c) includes actual productivity data for each individual member of a herd.

5. The method of herd management in accordance with claim 1, wherein the mathematical herd management model of step (b) comprises at least one equation that includes individual member adjustment factors that account for an individual member's productivity changes, resulting from effects based upon age, pregnancy, position on a lactation curve, a month of freshening and random and fixed residuals.

6. The method of herd management in accordance with claim 1, wherein the physical changes of step (e) include culling the less-productive members from a herd.

7. The method of herd management in accordance with claim 1, wherein the physical changes of step (e) include breeding the more productive members in a herd.

8. The method of herd management in accordance with claim 1, wherein the physical changes of step (e) include changing a herd's feed formulations to maximize milk production.

9. The method of herd management in accordance with claim 1, wherein the physical changes of step (e) include changing the environmental conditions in which a herd is housed.

10. A method of bovine herd management comprising the steps of:
    a) gathering data on milk production for each member of a herd on a routine basis;
    b) using a mathematical herd management model to modify the data to determine the actual productivity of each cow in the herd;
    c) establishing a database for each member of said herd, based upon the modified data of step (b);
    d) continuously updating said database;
    e) linking or combining said database with other like databases in order to make genetic evaluations and selections of primary, A-1 bulls that can sire daughters in many herds; and
    f) mating said primary, A-1 bulls with cows from different herds.

11. The method of herd management in accordance with claim 10, wherein said linking or combining step (e) comprises the linking and combining of databases of a plurality of herds nationwide.

12. The method of bovine herd management in accordance with claim 1, wherein said method can be used for genetically evaluating more than one herd.

13. A method of bovine herd management comprising the steps of:
    a) gathering data on milk production for each member of a herd on a routine basis;
    b) using a mathematical herd management model to modify the data to determine the actual productivity of each cow in the herd;
    c) establishing a database for each member of said herd, based upon the modified data of step (b);
    d) continuously updating said database;
    e) linking or combining said database with other like databases in order to make genetic evaluations and selections of genetically superior members of at least one herd; and
    f) mating said genetically superior members of said at least one herd.

14. The method of herd management in accordance with claim 13, wherein said linking or combining step (e) comprises the linking and combining of databases of a plurality of herds nationwide.

* * * * *

UNITED STATES PATENT AND TRADEMARK OFFICE
CERTIFICATE OF CORRECTION

PATENT NO. : 5,351,644
DATED : Oct. 4, 1994
INVENTOR(S) : Robert W. Everett

It is certified that error appears in the above-indentified patent and that said Letters Patent is hereby corrected as shown below:

Column 5, line 27:   delete multiplication symbol and substitute therefor an upper-case, capital "X"

Signed and Sealed this

Twenty-fourth Day of October, 1995

Attest:

BRUCE LEHMAN

Attesting Officer   Commissioner of Patents and Trademarks

REEXAMINATION CERTIFICATE (4042nd)

United States Patent
Everett

[11] B1 5,351,644
[45] Certificate Issued Apr. 18, 2000

[54] METHOD OF BOVINE HERD MANAGEMENT

[75] Inventor: Robert W. Everett, Freeville, N.Y.

[73] Assignee: Cornell Research Foundation, Inc., Ithaca, N.Y.

Reexamination Request:
No. 90/005,190, Dec. 16, 1998

Reexamination Certificate for:
Patent No.: 5,351,644
Issued: Oct. 4, 1994
Appl. No.: 08/023,244
Filed: Feb. 25, 1993

Certificate of Correction issued Oct. 24, 1995.

[51] Int. Cl.$^7$ .................................................. A01K 29/00
[52] U.S. Cl. ......................................... 119/14.01; 119/840
[58] Field of Search .............................. 119/14.01, 14.02, 119/51.01, 174, 840

[56] References Cited

PUBLICATIONS

K. Meyer, et al.; Estimates of Genetic Parameters for First Lactation Test Day Production of Australian Black & White Cows; Livestock Production Science, 21 (1989) 177–199.

Ali & Schaefer; Accounting for Covariances Among Test Day Milk Yields in Dairy Cows; Can J. Anim. Sci. 7: 637–644 (Sep. 1987).

Ptak & Schaefer; Use of test day yields for genetic evaluation of dairy sires & cows; Livestock Production Science, 34 (1993) pp. 23–34.

Bishop, et al.; Genetic evaluation of Canadian dairy goats test day data; 3 pages.

Stanton, et al.; Estimating Milk, Fat, and Protein Lactation Curves with a Test Day Model; J. Dairy Science vol. 75: 1691–1700.

Jones, et al.; Five Yrs. Experience with the animal model for dairy evaluations in Australia. pp. 382–385; Proceeding of the 4$^{th}$ world congress on genetic applied to livestock production; XIII Plenary Lectures, Molecular Genetics and Mapping, Selection, Prediction and Estimation, Edinburgh, Jul. 23–27, 1990.

Pander et al.; Genetic Parameters of Test Day Records of British Holstein–Friesian Heifers; Animal Products 55: 11–21; 1992.

*Primary Examiner*—Robert F. Swiatek

[57] ABSTRACT

A method of bovine herd management based upon a dynamic mathematical model. The method gathers data on milk production on a periodic or routine basis for each cow in the herd. The data includes factors denoting both the quantity and the quality of the milk being produced. A database for each cow is established and continuously updated. A mathematical herd management model is used to establish the database, wherein the gathered data is then modified and used to interpret and determine the actual productivity of each cow in the herd for that test day. Using this data, a manager of the herd can then breed those cows having a capability superior to their associates in the herd. Likewise, the less productive members of the herd can be culled or eliminated from the herd. Another aspect of the invention includes the use of the database to quantitatively assess the effect of change, including changes made in formulas, in environmental conditions and in breeding practices. Thus, for the first time, herd management can be scientifically controlled on a qantitative basis. Genetic evaluations can be made from the databases of many herds in order to select primary A-1, bulls capable of siring daughters in many herds. For maximum efficiency, databases of many herds can be combined or linked across the entire nation.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–14 is confirmed.

* * * * *